United States Patent [19]

Harrison et al.

[11] Patent Number: 4,738,794
[45] Date of Patent: Apr. 19, 1988

[54] AQUEOUS DISPERSION OF POTASSIUM SALT OF 4-SULPHO-PEROXYBENZOIC ACID STABILIZED WITH A POTASSIUM SALT

[75] Inventors: Paul R. Harrison; William R. Sanderson, both of Warrington, England

[73] Assignee: Interox Chemicals Limited, London, England

[21] Appl. No.: 894,278

[22] Filed: Aug. 7, 1986

[30] Foreign Application Priority Data

Aug. 7, 1985 [GB] United Kingdom ................. 8519799

[51] Int. Cl.$^4$ ................. C07C 179/133; C09K 15/02; C11D 7/38; C11D 7/54
[52] U.S. Cl. ................................. 252/186.26; 252/95; 252/99; 252/100; 252/102; 252/106; 252/174.17; 252/174.25; 252/DIG. 14; 260/502 R
[58] Field of Search ............... 260/502 R; 252/95, 99, 252/100, 102, 186.26, 106

[56] References Cited

U.S. PATENT DOCUMENTS

| | | | |
|---|---|---|---|
| 4,100,095 | 7/1978 | Hutchins | 252/99 |
| 4,391,725 | 7/1983 | Bossu | 252/90 |
| 4,529,534 | 7/1985 | Richardson | 252/110 |
| 4,536,313 | 8/1985 | Hignett | 252/100 |

FOREIGN PATENT DOCUMENTS

| | | | |
|---|---|---|---|
| 0124968 | 11/1984 | European Pat. Off. | |
| 6409889 | 8/1964 | Netherlands | 260/502 R |

*Primary Examiner*—Dennis Albrecht
*Attorney, Agent, or Firm*—Larson and Taylor

[57] ABSTRACT

Aqueous compositions containing an organic peroxyacid such as the mono-potassium salt of 4-sulpho-peroxybenzoic acid (KSPB) would be convenient to employ for bleaching/washing or disinfection especially of aqueous media, but suffer from loss of available oxygen (Avox) from the peracid during storage.

The problem of storage instability can be alleviated to a considerable extent by employing the KSPB in particulate form and incorporating in the aqueous phase a water-soluble potassium salt of a non-reducing acid having a pK$_a$ of below 6, preferably a non-halide. It is desirable to use at least 1% and preferably at least 5% w/w solution of the potassium salt, of which suitable examples are potassium sulphate and nitrate. The pH of the aqueous phase is preferably brought to pH 2 to 3.

38 Claims, No Drawings

AQUEOUS DISPERSION OF POTASSIUM SALT OF 4-SULPHO-PEROXYBENZOIC ACID STABILIZED WITH A POTASSIUM SALT

The present invention relates to peroxyacid compositions and more particularly to aqueous compositions, having improved storage stability.

Peroxyacids are typically of practical value as oxidising agents in organic synthesis, as bleaching agents and as disinfectants/biocides. In many of their applications, the medium into which they need to be introduced is aqueous. In addition, by virtue of their active oxygen content solid peroxyacids tend to be hazardous, to impact or thermal shock. In European Patent Specification No. 124968A, published Nov. 14, 1984 by Interox Chemicals Limited, there is described and claimed the mono-potassium salt of 4-sulpho-peroxybenzoic acid, KSPB. In order to minimise any hazard associated with the product, and to dose effectively into an aqueous medium, it would be especially convenient for the KSPB to be provided in an aqueous composition, but when such a composition was tried in a preliminary trial to the present invention, the KSPB lost its available oxygen by decomposition and equilibration more quickly than is preferred. This was not surprising in that the peracid was not only susceptible to decomposition induced by transition metals but reaction with water could freely take place via the step $R\text{-}CO_3H + H_2O = R\text{-}CO_2H + H_2O_2$. The equilibration step is undesirable since the resultant peroxygen species is less active under mild conditions of temperature and alkalinity than is the peracid. Unless otherwise indicated, the term storage stability hereinafter refers to the ability of a peracid to retain its available oxygen during storage.

In the case of solid peroxyacids, it was suggested that imrovements in the storage stability and/or desensitisation against impact or thermal shock of perphthalic acids could be achieved by mixing or coating the solid peroxyacids with a plethora of solid inorganic or organic substances including alkali or alkaline earth metal salts in British Patent Specification No. GBPS-1,085,787 to Pittsburgh Plate Glass Co. The best results were demonstrated in Tables 1 and 11 therein, employing sodium sulphate and magnesium sulphate. The same company in subsequent British Patent No. 1,112,778 advocated the use of solid hydrated salts including specifically hydrated magnesium and aluminium sulphates. The use of sodium and magnesium sulphate to stabilise organic peracids is endorsed by Procter and Gamble in U.S. Pat. No. 4,013,581 and in British Patent No. 1,456,592 the technique was stated to be applicable to aromatic and aliphatic peracids as such or further substituted by a range of acidic groups including a sulphonic acid group and water-soluble salt-forming cations thereof.

In view of the foregoing, it might be expected that when such salts are employed with KSPB an improvement would be noticeable in the rate at which it would lose its available oxygen, but unfortunately in aqueous compositions it has been found that the most widely praised salts, namely those of sodium and magnesium either have no beneficial effect, or even impair stability whilst addition of a soluble aluminum salt substantially impairs stability. However, it has been discovered that by selecting a water-soluble potassium salt the stability of KSPT in the aqueous system can be improved.

According to one aspect of the present invention there is provided a process for improving the storage stability of a dispersion of solid particulate 4-sulpho-peroxybenzoic acid, potassium salt in an aqueous acidic fluid characterised by introducing into the aqueous fluid one or more water-soluble non-reducing potassium salts of acids having a $pK_a$ of below 6, preferably other than halides.

According to a related aspect of the invention there is provided a composition having improved storage stability which comprises particulate 4-sulpho-peroxybenzoic acid, potassium salt, dispersed in an aqueous acidic phase containing a stabilising amount of one or more water-soluble non-reducing potassium salts of acids having a $pK_a$ of below 6, preferably other than halides.

The term "non-reducing" herein means that the salt anion is not oxidisable readily by an organic peroxyacid and accordingly salts such as sulphite, nitrite and ascorbate which otherwise would be suitable on solely solubility considerations are excluded.

Halides are preferably excluded from the invention composition and process in order to avoid a cycle in which the peracid oxidise the halide probably to an oxyhalide species which can react with any residual hydrogen peroxide with regeneration of the halide. Such a cycle can under normal storage temperatures accelerate the loss of available oxygen from KSPB.

The invention is applicable to any composition containing particulate KSPB, and an aqueous fluid in contact. In practice, particulate KSPB will normally comprise from 1 to 50% by weight of the composition and the aqueous phase the balance. The proportion of KSPB will often be selected by the formulator of the composition to provide a desired concentration of available oxygen after dilution in the bleach/washing liquor or in the aqueous medium to be disinfected. In many embodiments, the selection is likely to be in the range of 5 to 25% w/w particulate KSPB.

It has been found that the improvement in storage stability of KSPB increases progressively but non-linearly as the concentration of water-soluble potassium salt increases. Whilst a concentration of at least 0.1% w/w potassium salt results in some improvement, it is desirable to provide at least 0.5% w/w concentration and more preferably at least 2% w/w. Any solution up to a saturated solution of the water-soluble salt in the presence of undissolved salt can be used, if desired, but in practice the greater part of the benefit is typically achieved without exceeding 10% w/w concentration. Accordingly, in some highly preferred embodiments the concentration of the soluble potassium salt is 5 to 10% w/w.

The soluble potassium salt can be any salt that delivers the desired proportion of potassium into solution and meets the twin requirements of an appropriate $pK_a$ and non-reducibility, although for the reason outlined earlier it is highly desirable to avoid halides. It is especially convenient to use inorganic salts such as the sulphate or nitrate, or meta, ortho or pyrophosphate. Other inorganic salts, which can be tolerated to the extent that the solution remains acidic, include borate and carbonate. Organic salts which can be contemplated include acetate, formate, citrate, tartrate, propionate and sorbate. A further group of suitable organic salts comprises benzoate and benzene sulphonate, each optionally substituted by one or more methyl, halt, nitro or carboxylic acid/anion groups, such as p-toluene sulphonate and 4-sulphobenzoate. It is also highly advisable to avoid salts of oxyacids of transition metals such as chromate or vanadate, thereby avoiding introduction of decomposition catalysts for peroxy compounds. The aqueous phase usually is maintained at a pH of below pH 5 but above pH 1, typically from pH 2 to 3 and in many instances from pH 2.4 to 2.8.

In the absence of any other additives the composition has the form of a particulate solid that has settled beneath an aqueous acidic potassium solution. However, the form can be altered by incorporating into the composition a small amount of one or more water-soluble or insoluble thickener whereby the phase is thickened to a viscous fluid, in which the solid particles can be suspended if enough thickener is employed. The amount of thickener to add is at the discretion of the formulator and will depend also upon the nature of the thickener as well as the concentration of potassium salt and any other solute in the aqueous phase and particle size of the suspended KSPB. Thickeners worthy of appraisal by the formulator include gums such as alginates, carrageenans (sulphated polysaccharides from seaweeds) plant gums such as tragacanth and guar gum, and microbially produced gums such as dextran and especially xanthan gum. Two or more gums can be used such as xanthan/guar gum mixtures. Other organic thickeners include starches and modified starches including acid-modified and heat-treated starches, and starch derivatives including cationic starches. Inorganic thickeners that can be considered include colloidal silicas and silicates, bentonites, talc, modified magnesium aluminosilicates such as available under the Trade Mark VEE-GUM of R. T. Vanderbilt and synthetic hydrous magnesium silicates as available under the Trade Mark LAPONITE of Laporte Industries Ltd. Typical amounts are less than 2% w/w.

In addition, the aqueous phase can also include one or more additives that assist in washing bleaching or disinfection. Of these, one class comprises surfactants, including anionic, nonionic and zwitterionic surfactants to assist wetting and cationic surfactants many of which can assist disinfection. In total the surfactants normally comprise less than 40% w/w of the composition and where the composition is strictly formulated as a bleach additive then it represents typically less than 10% w/w. Amongst surfactants of interest must be included alkyl aryl sulphonates, especially C12 approx benzene sulphonates, fatty alcohol sulphates, olefine sulphates and sulphonates, sulphated glycerides, sulphated ethers, sulphosuccinates, alkane sulphonates and phosphate esters. Amongst nonionic surfactants of importance are condensates of ethylene and/or propylene oxide, especially with fatty alcohols, fatty acids or fatty amines or amides. It will be recognised that combinations of fatty acis alkanolamides and alkyl benzene sulphonates can increase substantially the viscosity of the aqueous phase, thereby acting as surfactant and thickener combined. Amongst cationic surfactants, quaternary ammonium compounds are of interest, especially when at least one of the substituents is long chain such as cetyl and/or two combined to form a pyridinium moiety.

Other optional components of the composition can comprise minor amounts of soil anti-redeposition agents, optical brightening agents and organic peracid stabilisers.

The compositions can be prepared by mixing the solid ingredients, the aqueous phase and any non-aqueous liquid in any order, but care is preferably taken to ensure that the aqueous phase remains acidic in the presence of KSPB.

For storage and easy use, the compositions may conveniently be incorporated in pouches, sachets or bottles. They can be employed in the appropriate amounts to provide the desired peracid available oxygen and for the same purposes and the same physical conditions described in the aforesaid European Patent Specification No. 12498A on pages 15 to 18, that is to say as bleach additives, in disinfection/sanitisation and cleansing of hard surfaces.

Having described the invention in general terms, specific examples will be described more fully by way of example.

COMPARISON 1 AND EXAMPLES 2 TO 6

In this Comparison and Examples, 10% w/w particulate KSPB was mixed with 90% w/w water or aqueous solutions of potassium sulphate having the concentrations shown in Table 1 below. The bottles containing the resultant mixtures were shaken by hand each weekday and stored at 32° C. and the available oxygen from the peracid was measured initially and after respectively 8 and 16 weeks storage. The resultant figures are compared and presented as the % Avox lost during storage the total available oxygen in the compositions was likewise measured and by comparison between that and the peracid available oxygen, the residual $H_2O_2$ level was measured. A—in the Table indicates that no measurement was made.

TABLE 1

| Comp/ | Conc $K_2SO_4$ | % Avox Lost | | % $H_2O_2$ |
| --- | --- | --- | --- | --- |
| Ex | % w/w | 8 wks | 16 wks | level |
| C1 | 0 | 43 | 69 | 0.10 |
| Ex2 | 0.9 | 25 | 34 | 0.05 |
| Ex3 | 1.8 | 20 | 29 | 0.04 |
| Ex4 | 4.5 | — | 21 | — |
| Ex5 | 6.3 | 13 | 18 | 0.02 |
| Ex6 | 9.0 | 9 | 17 | 0.02 |

From Table 1, it can be seen that the loss of Avox from KSPB becomes progressively lower as the concentration of potassium sulphate in the aqueous phase increases, and that it was only partly retained as $H_2O_2$.

COMPARISONS C7 TO C11 AND EXAMPLES 12, 13

In these Comparisons and Examples, further samples of KSPB (10% w/w) were mixed with 90% w/w water or the aqueous solution containing 0.25 moles of the salt (measured as the cation) specified in Table 2. The compositions were shaken and stored at 32° C. as in the preceding Examples. The initial and residual % Avox from KSPB in the compositions was likewise measured and compared.

TABLE 2

| Comp/ | | % Avox Lost | |
| --- | --- | --- | --- |
| Ex | Salt | 8 wks | 16 wks |
| C7 | — | 21 | 40 |
| C8 | $Na_2SO_4$ | 26 | 53 |
| C9 | $MgSO_4$ | 39 | 66 |
| C10 | $CaSO_4$ | 30 | 48 |
| C11 | $Al_2(SO_4)_3$ | 57 | 91 |
| Ex12 | $K_2SO_4$ | 2 | 21 |
| Ex13 | $KNO_3$ | 10 | 16 |

From Table 2, it can be seen that the sodium, magnesium, calcium and aluminium salts did not improve the stability of KSPB of storage whereas the addition of both potassium sulphate and nitrate significantly improved the stability.

We claim:

1. A composition having improved storage stability which comprises 1-50% by weight of particulate 4-sulpho-peroxybenzoic acid, potassium salt in an aqueous acidic phase having a pH of more than 1 and less than 5 and containing a stabilising amount of one or more water-soluble non-reducing potassium salts of acids having a $pK_a$ of below 6.

2. A composition according to claim 1 in which the non-reducing potassium salt employed is other than a halide.

3. A composition according to claim 1 or 2 in which the non-reducing potassium salt is employed in an amount of at least 0.1% w/w of the composition.

4. A composition according to claim 3 in which the amount of non-reducing potassium salt is at least 2% w/w.

5. A composition according to claim 3 in which the amount the non-reducing potassium salt is from 5 to 10% w/w of the composition.

6. A composition according to claim 1 or 2 in which the non-reducing potassium salt is selected from phosphate, sulphate, nitrate, acetate, formate, citrate, tartrate, propionate and sorbate, and benzene sulphonate or benzoate, either unsubstituted or optionally substituted by one or more methyl, halo, nitro or carboxylic acid/carboxylate groups.

7. A composition according to claim 6 in which the non-reducing potassium salt is selected from sulphate and nitrate.

8. A composition according to claim 1 or 2 in which the potassium salt of 4-sulpho-peroxybenzoic acid comprises 5 to 25% w/w of the aqueous acidic phase.

9. A composition according to claim 1 wherein said pH is from pH 2 to 3.

10. A process for improving the storage stability of an aqueous composition comprising 1-50% by weight of solid particulate 4-sulpho-peroxybenzoic acid, potassium salt in an aqueous acidic fluid, said aqueous acidic fluid having a pH of more than 1 and less than 5, comprising introducing into the aqueous fluid a stabilizing amount of one or more water-soluble non-reducing potassium salts of acids having a $pK_a$ of below 6.

11. A process according to claim 10 in which the non-reducing potassium salt employed is other than a halide.

12. A process according to claim 10 or 11 in which the non-reducing potassium salt is employed in an amount of at least 0.1% w/w of the composition.

13. A process according to claim 12 in which the amount of the non-reducing potassium salt is from 5 to 10% w/w of the composition.

14. A process according to claim 12 in which the non-reducing potassium salt is employed in an amount of at least 2% w/w.

15. A process according to claim 10 or 11 in which the non-reducing potassium salt is selected from phosphate, sulphate, nitrate, acetate, formate, citrate, tartrate, propionate and sorbate, and benzene sulphonate or benzoate, either unsubstituted or optionally substituted by one or more methyl, halo, nitro or carboxylic acid/carboxylate groups.

16. A process according to claim 15 in which the non-reducing potassium salt is selected from sulphate and nitrate.

17. A process according to claim 10 or 11 in which the potassium salt of 4-sulpho-peroxybenzoic acid comprises 5 to 25% w/w of the aqueous acidic fluid.

18. A process according to claim 10 wherein said pH is from pH 2 to 3.

19. A composition having improved storage stability which comprises 1-50% by weight of particulate 4-sulpho-peroxybenzoic acid, potassium salt dispersed in an aqueous acidic phase containing a thickening agent in an amount sufficient to maintain said peroxybenzoic acid salt in suspension and containing a stabilising amount of one or more water-soluble non-reducing potassium salts of acids having a $pK_a$ of below 6.

20. A composition according to claim 19 in which the non-reducing potassium salt employed is other than a halide.

21. A composition according to claim 19 or 20 in which the non-reducing potassium salt is employed in an amount of at least 0.1% w/w of the composition.

22. A composition according to claim 21 in which the amount of non-reducing potassium salt is at least 2% w/w.

23. A composition according to claim 21 in which the amount the non-reducing potassium salt is from 5 to 10% w/w of the composition.

24. A composition according to claim 19 or 20 in which the non-reducing potassium salt is selected from phosphates, sulphate, nitrate, acetate, formate, citrate, tartrate, propionate and sorbate, and benzene sulphonate or benzoate, either unsubstituted or optionally substituted by one or more methyl, halo, nitro or carboxylic acid/carboxylate groups.

25. A composition according to claim 24 in which the non-reducing potassium salt is selected from sulphate and nitrate.

26. A composition according to claim 19 or 20 in which the aqueous phase is brought to a pH of below pH 5.

27. A composition according to claim 26 wherein said pH is from pH 2 to 3.

28. A composition according to claim 2 or 13 in which the potassium salt of 4-sulpho-peroxybenzoic acid comprises 5 to 25% w/w of the aqueous acidic phase.

29. A process for improving the storage stability of a dispersion of 1-50% by weight of solid particulate 4-sulpho-peroxybenzoic acid, potassium salt in an aqueous acidic fluid, said dispersion containing a thickening agent in an amount sufficient to maintain said peroxybenzoic acid salt in suspension, comprising introducing into the aqueous fluid a stabilizing amount of one or more water-soluble non-reducing potassium salts of acids having a $pK_a$ of below 6.

30. A process according to claim 1 in which the non-reducing potassium salt employed is other than a halide.

31. A process according to claim 29 or 30 in which the nonreducing potassium salt is selected from phosphates, sulphate, nitrate, acetate, formate, citrate, tartrate, propionate and sorbate, and benzene sulphonate or benzoate, either unsubstituted or optionally substituted by one or more methyl, halo, nitro or carboxylic acid/carboxylate groups.

32. A process according to claim 31 in which the non-reducing potassium salt is selected from sulphate and nitrate.

33. A process according to claim 29 or 30 in which the aqueous phase is brought to a pH of below pH 5.

34. A process according to claim 33 wherein said pH is from pH 2 to 3.

35. A process according to claim 1 or 3 in which the non-reducing potassium salt is employed in an amount of at least 0.1% w/w of the composition.

36. A process according to claim 30 in which the amount of the non-reducing potassium salt is from 5 to 10% w/w of the composition.

37. A process according to claim 35 in which the non-reducing potassium salt is employed in an amount of at least 2% w/w.

38. A process according to claim 1 or 3 in which the potassium salt of 4-sulpho-peroxybenzoic acid comprises 5 to 25% w/w of the aqueous acidic fluid.

* * * * *